(12) United States Patent
Umekawa et al.

(10) Patent No.: US 11,282,244 B2
(45) Date of Patent: Mar. 22, 2022

(54) MOVING BODY TRACKING APPARATUS, RADIATION THERAPY SYSTEM INCLUDING THE SAME, PROGRAM, AND MOVING BODY TRACKING METHOD

(71) Applicants: Hitachi, Ltd., Tokyo (JP); NATIONAL UNIVERSITY CORPORATION HOKKAIDO UNIVERSITY, Sapporo (JP)

(72) Inventors: Toru Umekawa, Tokyo (JP); Koichi Miyazaki, Tokyo (JP); Takaaki Fujii, Tokyo (JP); Shinichi Shimizu, Sapporo (JP); Seishin Takao, Sapporo (JP); Kikuo Umegaki, Sapporo (JP); Naoki Miyamoto, Sapporo (JP); Norio Katoh, Sapporo (JP)

(73) Assignees: HITACHI, LTD., Tokyo (JP); NATIONAL UNIVERSITY CORPORATION HOKKAIDO UNIVERSITY, Sapporo (JP)

( * ) Notice: Subject to any disclaimer, the term of this patent is extended or adjusted under 35 U.S.C. 154(b) by 149 days.

(21) Appl. No.: 16/783,206

(22) Filed: Feb. 6, 2020

(65) Prior Publication Data
US 2020/0311988 A1 Oct. 1, 2020

(30) Foreign Application Priority Data
Mar. 25, 2019 (JP) .............................. JP2019-056069

(51) Int. Cl.
*G06K 9/00* (2006.01)
*G06T 11/00* (2006.01)
(Continued)

(52) U.S. Cl.
CPC .......... *G06T 11/008* (2013.01); *G06T 7/0014* (2013.01); *G06T 7/20* (2013.01);
(Continued)

(58) Field of Classification Search
CPC ....... G06T 11/008; G06T 7/70; G06T 7/0014; G06T 7/20; G06T 2207/10064; G06T 2207/10076
See application file for complete search history.

(56) References Cited

U.S. PATENT DOCUMENTS

2017/0231586 A1 8/2017 Hirai et al.
2018/0154180 A1* 6/2018 Mori .................... A61B 6/4266
(Continued)

FOREIGN PATENT DOCUMENTS

JP 2008-154861 A 7/2018
WO 2018/168766 A1 9/2018

OTHER PUBLICATIONS

Extended European Search Report received in corresponding European Application No. 20158275.6 dated Jun. 15, 2020.

*Primary Examiner* — Atiba O Fitzpatrick
(74) *Attorney, Agent, or Firm* — Mattingly & Malur, PC

(57) ABSTRACT

Provided are a moving body tracking apparatus that contributes to shortening treatment time and a radiation therapy system including the moving body tracking apparatus, a program, and a moving body tracking method. The moving body tracking apparatus includes a fluoroscopic apparatus that acquires fluoroscopic images including the target 2 from at least two directions, and the moving body tracking control apparatus 30A that obtains a position of the target 2 from the fluoroscopic images acquired by the fluoroscopic apparatus. The moving body tracking control apparatus 30A creates a simulated fluoroscopic image from the CT image including the target 2, creates a two-dimensional region including the target 2 from the simulated fluoroscopic image as a template, matches each of at least two fluoroscopic images with the template, and obtains a three-dimensional position of the target 2 from a plurality of matching results.

11 Claims, 5 Drawing Sheets

(51) Int. Cl.
*G06T 7/70* (2017.01)
*G06T 7/00* (2017.01)
*G06T 7/20* (2017.01)

(52) U.S. Cl.
CPC ...... *G06T 7/70* (2017.01); *G06T 2207/10064* (2013.01); *G06T 2207/10076* (2013.01)

(56) References Cited

U.S. PATENT DOCUMENTS

2019/0005687 A1* 1/2019 Weingarten ............. G06T 19/00
2019/0060672 A1   2/2019 Takahashi et al.
2020/0069967 A1* 3/2020 Mori ................... A61B 6/4429

* cited by examiner

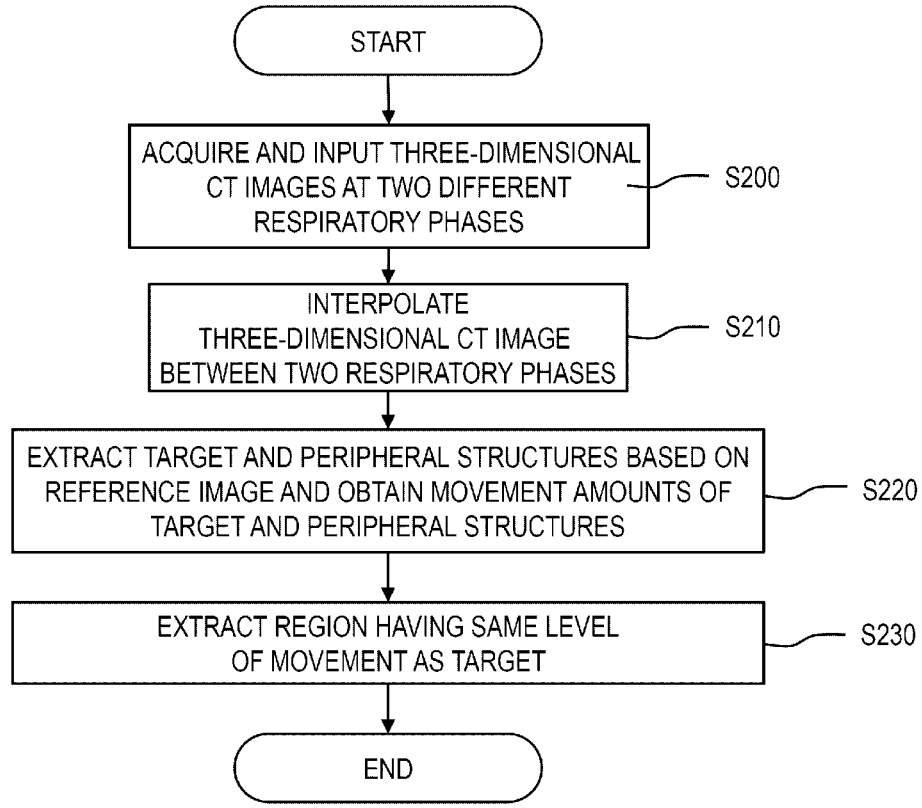
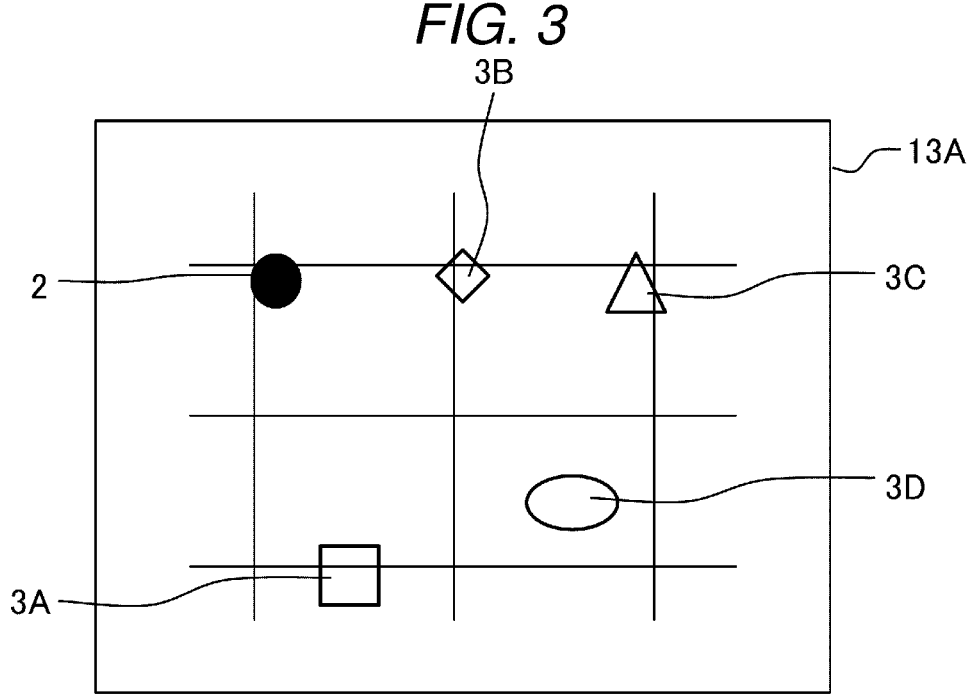

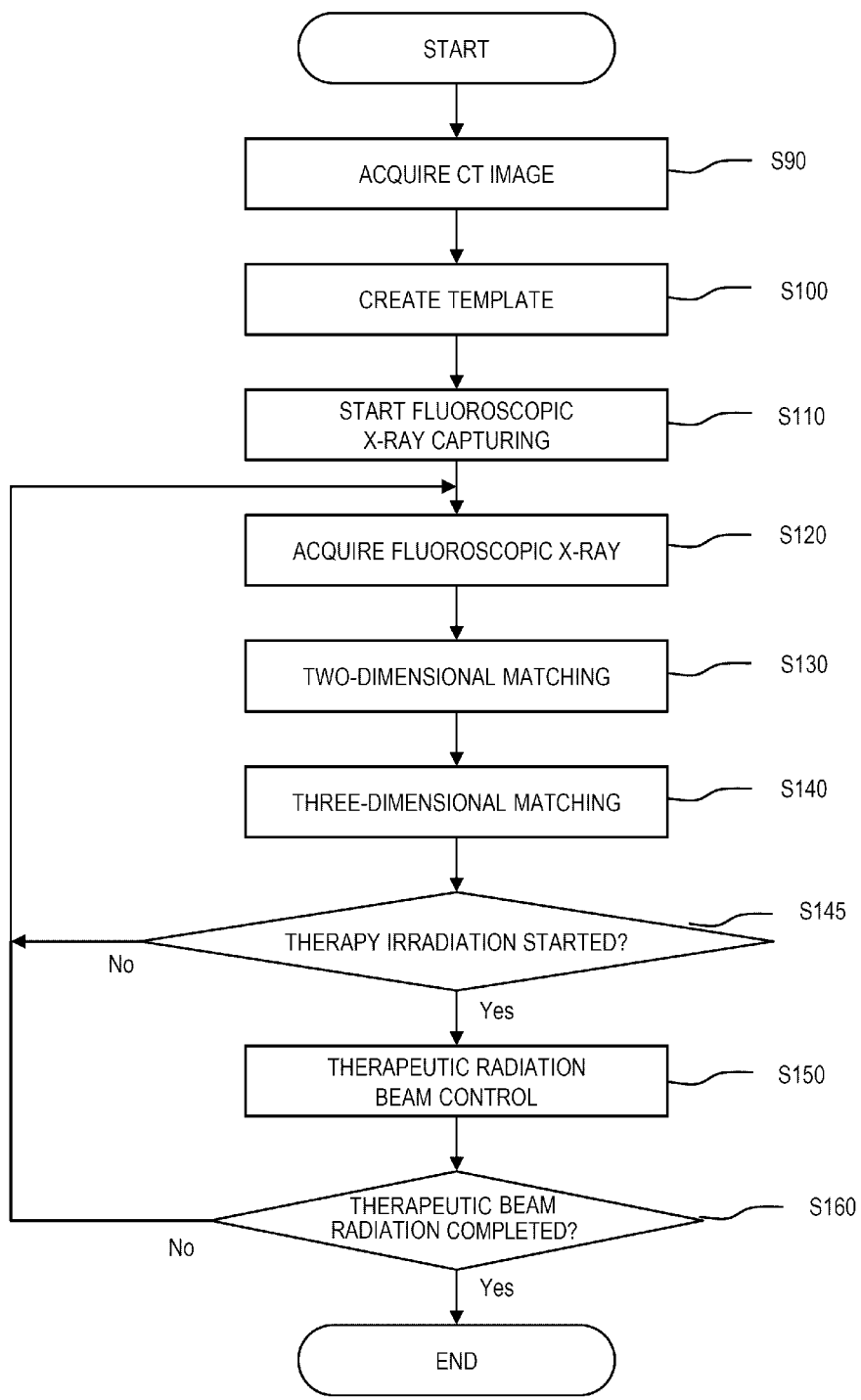

MOVING BODY TRACKING APPARATUS, RADIATION THERAPY SYSTEM INCLUDING THE SAME, PROGRAM, AND MOVING BODY TRACKING METHOD

CROSS-REFERENCE TO RELATED APPLICATION

The present application claims priority from Japanese application JP 2019-056069, filed on Mar. 25, 2019, the contents of which is hereby incorporated by reference into this application.

BACKGROUND OF THE INVENTION

1. Field of the Invention

The present invention relates to a moving body tracking apparatus and a moving body tracking program suitable for a radiation therapy system that recognizes a target position and controls irradiation, and a moving body tracking method.

2. Description of the Related Art

JP-A-2008-154861 (Patent Literature 1) discloses a radiation therapy system that accurately irradiates a therapeutic target portion such as a tumor whose position periodically changes due to breathing of a human body with a therapeutic radiation. In Patent Literature 1, the radiation therapy system includes a human body capturing apparatus and a therapeutic radiation irradiation apparatus. When a therapy of the therapeutic target portion such as a tumor in the human body is performed, a fluoroscopic image of the inside of a human body is generated over time by the human body capturing apparatus. When image information of the fluoroscopic image generated over time substantially matches image information of a reference fluoroscopic image in a specific respiratory phase generated in advance, the therapeutic radiation is radiated to the therapeutic target portion in the human body by the therapeutic radiation irradiation apparatus.

In radiation therapy that irradiates a target in a body with the therapeutic radiation, in order to precisely irradiate the target with the therapeutic radiation, it is necessary to cope with movement of the target due to breathing or the like.

As a method for coping with the movement, there is known a method of capturing an X-ray fluoroscopic image in real time, obtaining a target position from the captured image, and controlling a therapeutic radiation in accordance with the obtained target position, for example, the method described in Patent Literature 1.

In Patent Literature 1, a three-dimensional CT image is captured in a state in which the therapeutic radiation is to be radiated before therapy, a projection image is created from the CT image, and the therapeutic radiation is radiated when an X-ray fluoroscopic image captured during the therapy matches the projection image. Accordingly, the therapeutic radiation can be precisely radiated to the target since the therapeutic radiation is radiated only when the target is in a position where the therapeutic radiation is to be radiated.

The method of Patent Literature 1 can be applied even when the target is difficult to visually recognize in the X-ray fluoroscopic image. In Patent Literature 1, since the three-dimensional CT image is captured immediately before therapy, positional relationships between the target and a peripheral structure during CT image capture and during the therapy can be expected to match. Therefore, even when the target is difficult to be visually recognized by both the projection image and the X-ray fluoroscopic image, it is expected that target positions would also match when peripheral structures match.

Since a tumor is difficult to be visually recognized in an X-ray apparatus image, a marker or the like is inserted so that the tumor is visualized. In contrast, when the above method is used, a tumor position can be determined without a marker.

Here, in the technique described in Patent Literature 1, it is determined whether the target is in a position to be radiated based on a degree of matching between the projection image and the X-ray fluoroscopic image. Therefore, although it can be determined that the images are completely matched, there is no way of knowing how much the degree of matching of the images is reduced when the target moves and deviates.

On the other hand, there is no way of knowing how much the target is deviated when the degree of matching of the images reduces. In order to precisely irradiate the target with the therapeutic radiation, it is necessary to narrow down an allowable width of the degree of matching so that the deviation of the target would be greatly small. However, in this case, timing at which the therapeutic radiation can be radiated within a respiratory cycle is greatly small, and it is necessary to perform irradiation over a large number of respiratory cycles. That is, treatment time is long.

SUMMARY OF THE INVENTION

An object of the invention is to provide a moving body tracking apparatus contributing to shortening treatment time, a radiation therapy system including the moving body tracking apparatus, a moving body tracking program, and a moving body tracking method.

The invention includes a plurality of ways for solving the above problems and an example thereof is a moving body tracking apparatus that obtains a three-dimensional position of a target and tracks movement of the target. The moving body tracking apparatus includes a fluoroscopic apparatus that acquires fluoroscopic images including the target from at least two directions; and a moving body tracking control apparatus that obtains a position of the target from the fluoroscopic images acquired by the fluoroscopic apparatus. The moving body tracking control apparatus creates a simulated fluoroscopic image from a CT image including the target, creates a two-dimensional region including the target from the simulated fluoroscopic image as a template, matches each of at least two or more fluoroscopic images with the template, and obtains the three-dimensional position of the target from a plurality of matching results.

The invention can contribute to shortening treatment time. Problems, configurations, and effects other than the above ones will become apparent from the following description of an embodiment.

BRIEF DESCRIPTION OF THE DRAWINGS

FIG. 2 is a flowchart illustrating a flow of processing of two-dimensional template creation by the moving body tracking apparatus according to the embodiment;

FIG. 3 is a diagram illustrating an outline of the two-dimensional template creation by the moving body tracking apparatus according to the embodiment;

FIG. 8 is a flowchart showing a processing procedure of a radiation by the radiation therapy system including a moving body tracking method according to the embodiment.

DESCRIPTION OF THE PREFERRED EMBODIMENTS

An embodiment of a moving body tracking apparatus and a radiation therapy system including the moving body tracking apparatus, a program, and a moving body tracking method according to the invention will be described with reference to FIGS. 1 to 8.

Figure 1:
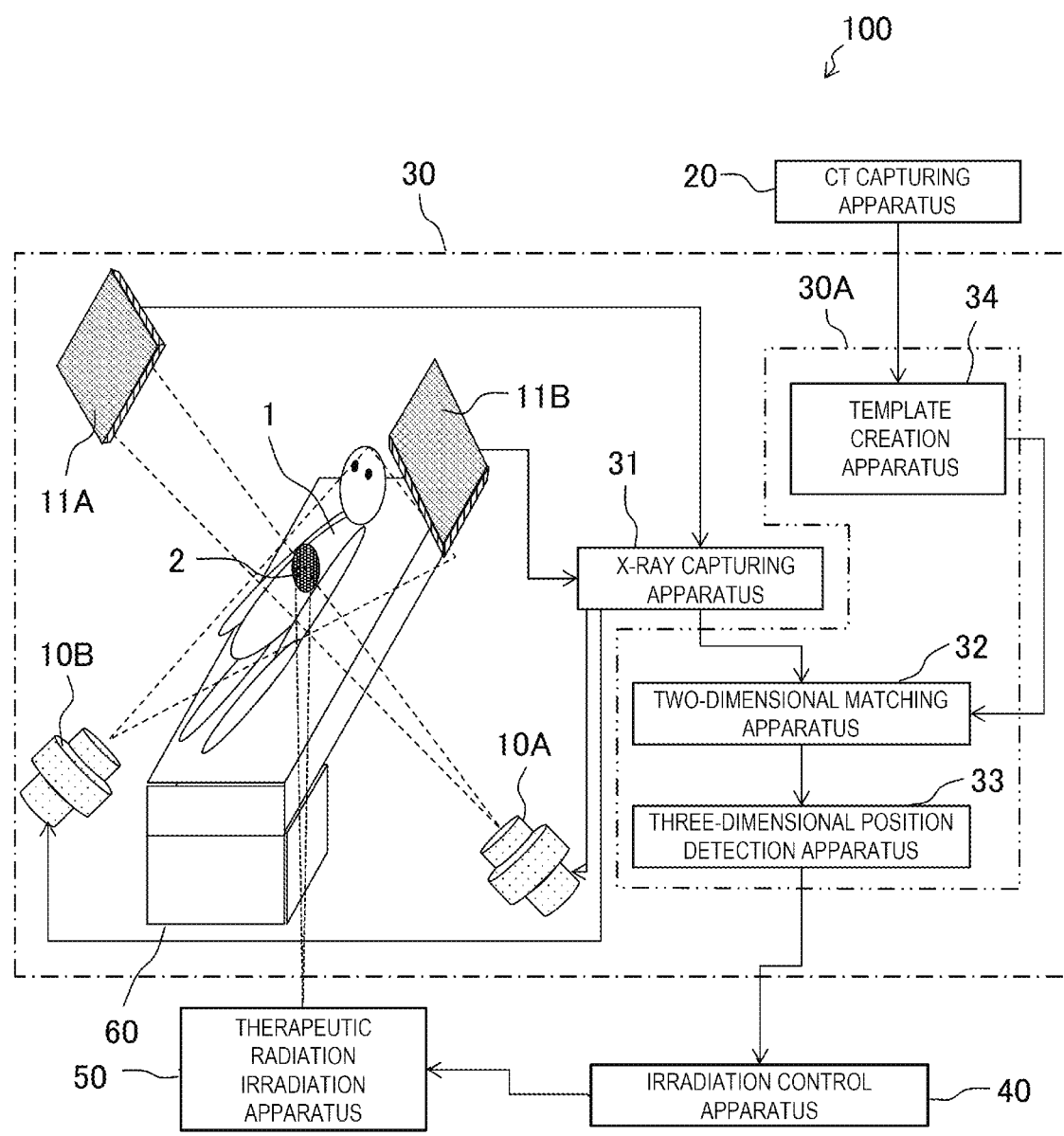
FIG. 1 is a diagram showing a schematic configuration of a radiation therapy system and a moving body tracking apparatus according to an embodiment of the invention.

First, an overall configuration of a radiation therapy system 100 will be described with reference to FIG. 1. FIG. 1 is a diagram showing a schematic configuration of a radiation therapy system according to the present embodiment.

In FIG. 1, the radiation therapy system 100 is an apparatus for irradiating a target volume (hereinafter referred to as a target 2) in a patient (hereinafter referred to as a "subject 1") with a therapeutic radiation. The therapeutic radiation used is, for example, a particle beam including protons or heavy particles such as carbon, a therapeutic X-ray, a therapeutic γ ray, and a therapeutic electron beam. In the following description, a case where the particle beam is used as a therapeutic radiation will be described.

In the invention, tracking markers are not pre-filled in the subject 1 to track the target 2 in the subject 1.

The radiation therapy system 100 includes a bed 60 capable of positioning the subject 1, a CT capturing apparatus 20, a moving body tracking apparatus 30, a therapeutic radiation irradiation apparatus 50 that generates particle beams and irradiates the target 2 in the subject 1, and an irradiation control apparatus 40, and the like.

The therapeutic radiation irradiation apparatus 50 includes an accelerator, a beam transport system, and an irradiation apparatus (none of them are shown). A therapeutic particle beam is accelerated to necessary energy by the accelerator provided in a room separated from a therapy room, and then guided to the beam transport apparatus. The accelerator may be a synchrotron accelerator, a cyclotron accelerator, or various other accelerators.

The irradiation apparatus in the therapeutic radiation irradiation apparatus 50 includes two pairs of scanning electromagnets, a dose monitor, and a position monitor (none of them are shown). The two pairs of scanning electromagnets are arranged in directions orthogonal to each other, and can deflect particle beams so that the particle beams reach a desired position in a plane perpendicular to a beam axis in a target position. The dose monitor measures an amount of radiated particle beams. The position monitor can detect a position through which the particle beams have passed. The particle beams from the therapeutic radiation irradiation apparatus 50 reach the target 2.

A method of radiating the particle beams is not particularly limited. In addition to a spot scanning method that forms dose distribution corresponding to a shape of the target 2 by arranging dose distribution formed by fine particle beams, a raster scanning method or a line scanning method in which fine particle beams are radiated without stopping the particle beams can be used.

In addition to the scanning methods described above, the invention can also be applied to an irradiation method that forms dose distribution corresponding to a shape of a target using a collimator or a bolus after expanding the particle beam distribution, such as a wobbler method or a double scatterer method.

The invention can also be applied to tracking irradiation in which an irradiation position is changed in accordance with movement of the target 2.

When an X-ray is used instead of the particle beams such as a carbon beam or a proton beam as a therapeutic radiation, a therapy X-ray irradiation apparatus that generates a therapeutic X-ray instead of the accelerator or the beam transport apparatus is provided. When a γ-ray is used, a γ-ray irradiation apparatus that generates a therapeutic γ-ray instead of the accelerator or the beam transport apparatus is provided. When an electron beam is used, an electron beam irradiation apparatus that generates a therapeutic electron beam instead of the accelerator or the beam transport apparatus is provided.

The CT capturing apparatus 20 is constituted such that a three-dimensional CT image of the subject 1 lying on the bed 60 can be captured. Preferably, the CT capturing apparatus 20 is installed in a therapy room where the bed 60 is installed. By capturing CT at different time phases by the CT capturing apparatus 20, a four-dimensional CT image is acquired. Since the CT capturing apparatus 20 is provided in the radiation therapy system 100, it is possible to perform three-dimensional CT capturing or four-dimensional CT capturing immediately before therapy.

The moving body tracking apparatus 30 is an apparatus that obtains a three-dimensional position of the target 2 and tracks movement thereof, and includes a fluoroscopic apparatus that acquires X-ray fluoroscopic images including the target 2 from at least two directions, and a moving body tracking control apparatus 30A that obtains a position of the target from the X-ray fluoroscopic images acquired by the fluoroscopic apparatus.

The fluoroscopic apparatus includes an X-ray tube 10A that generates fluoroscopic X-rays from a first direction toward the target 2 in the subject 1, a detector 11A that detects two-dimensional dose distribution of the fluoroscopic X-rays generated from the X-ray tube 10A and transmitted through the subject 1, an X-ray tube 10B that generates fluoroscopic X-rays from a second direction different from the first direction toward the subject 1, a detector 11B that detects two-dimensional dose distribution of the fluoroscopic X-rays generated from the X-ray tube 10B and transmitted through the subject 1, and an X-ray capturing apparatus 31 including a signal processing circuit.

The detectors 11A and 11B output analog signals from two-dimensionally arranged detection elements.

The X-ray capturing apparatus 31 instructs the X-ray tubes 10A and 10B to radiate transmission X-rays, processes the analog signals from the detectors 11A and 11B, generates X-ray fluoroscopic image data, and transmits the data to a two-dimensional matching apparatus 32 of the moving body tracking control apparatus 30A.

In the present embodiment, there are two capturing directions by the X-rays of the fluoroscopic apparatus. However, the capturing directions are not limited to two, and may be any directions equal to two or more, and an X-ray tube and a detector can be appropriately added.

The moving body tracking control apparatus 30A is an apparatus that calculates a position of the target 2 based on a signal of an X-ray fluoroscopic image input from the fluoroscopic apparatus, and outputs the calculated position of the target 2 to the irradiation control apparatus 40.

As shown in FIG. 1, the moving body tracking control apparatus 30A includes a template creation apparatus 34, the two-dimensional matching apparatus 32, and a three-dimensional position detection apparatus 33.

The template creation apparatus 34 creates a simulated X-ray fluoroscopic image from a CT image including the target 2, and forms an image of a two-dimensional region including the target 2 from the simulated X-ray fluoroscopic image as a template image.

More specifically, the template creation apparatus 34 receives an input of two or more three-dimensional CT images (four-dimensional CT images) captured by the CT capturing apparatus 20 and figures out, according to arrangements of the X-ray tubes 10A and 10B and the detectors 11A and 11B controlled by the X-ray capturing apparatus 31, a projection image simulating an X-ray fluoroscopic image captured by the X-ray tubes 10A and 10B and the detectors 11A and 11B from each of the two or more three-dimensional CT images.

At this time, a plurality of projection images are created corresponding to a plurality of X-ray tubes 10A and 10B and the detectors 11A and 11B. In the obtained projection images, a place where the target 2 to be treated in a body of the subject 1 is photographed is specified, and a peripheral portion thereof is extracted as a template image serving as a reference image of the target 2 at the time of matching.

Figure 4:
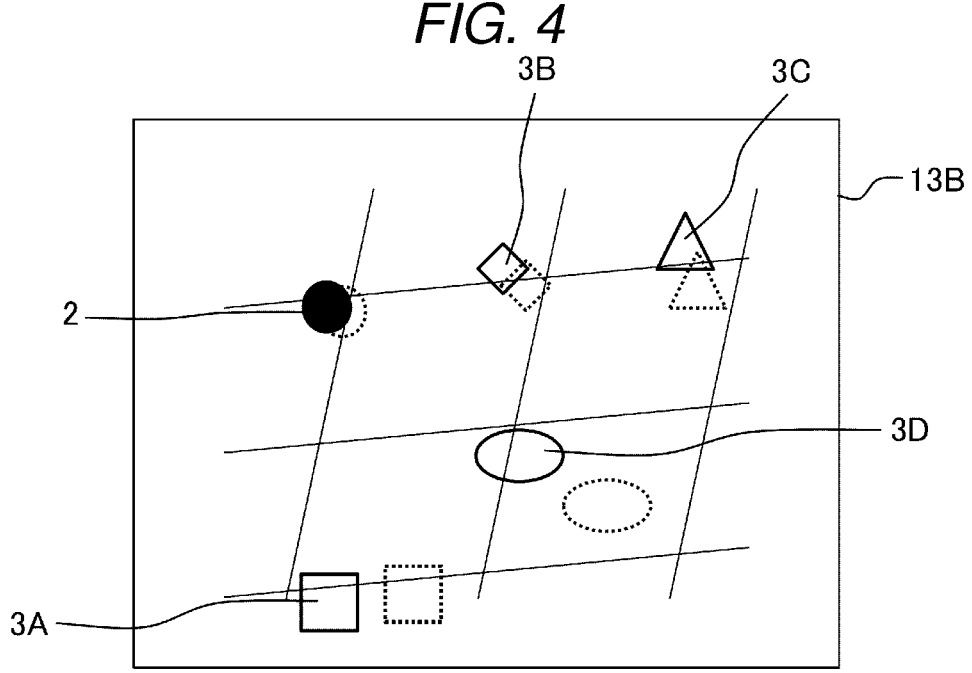
FIG. 4 is a diagram illustrating an outline of the two-dimensional template creation by the moving body tracking apparatus according to the embodiment.
Figure 5:
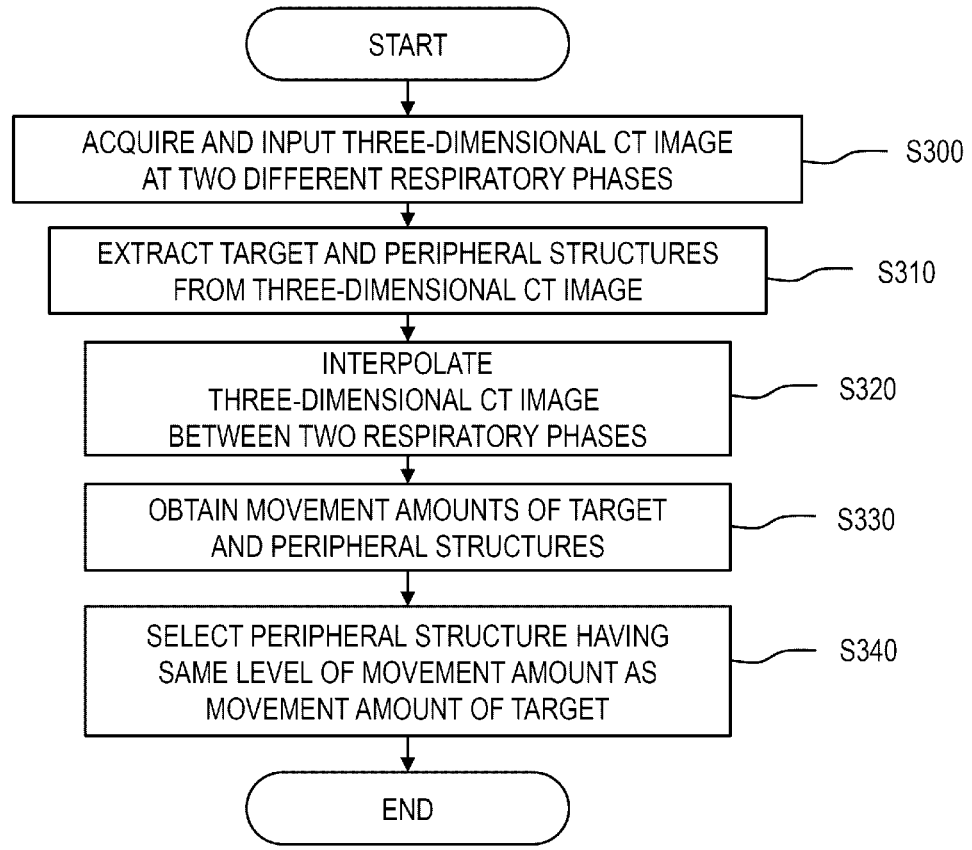
FIG. 5 is a flowchart illustrating another example of a flow of processing of two-dimensional template creation by the moving body tracking apparatus according to the embodiment.

A flow of creating a template by the template creation apparatus 34 will be described below with reference to FIGS. 2 to 5. FIG. 2 is a flowchart illustrating a flow of processing of two-dimensional template creation. FIGS. 3 and 4 are diagrams illustrating outlines of the two-dimensional template creation processing. FIG. 5 is a flowchart illustrating another example of a flow of processing of two-dimensional template creation.

As shown in FIG. 2, first, the template creation apparatus 34 receives an input of three-dimensional CT images (four-dimensional CT images) acquired at two different respiratory phases (step S200).

After that, the template creation apparatus 34 performs deformation positioning by associating reference positions of the two three-dimensional CT images and interpolating a three-dimensional CT image between the two respiratory phases (step S210). An interpolation method is not particularly limited, and various known methods can be used.

Next, the template creation apparatus 34 extracts the target 2 and peripheral structures based on a reference image, and obtains movement amounts of the target 2 and the peripheral structures (step S220).

Since the movement amounts of the target 2 and the peripheral structures are known in the previous step S220, the template creation apparatus 34 extracts, as a tracking peripheral structure, a peripheral structure, among the peripheral structures, that has the same level of movement as the target 2, for example, a peripheral structure in which a difference between the calculated movement amount of the target 2 and the movement amount of the peripheral structure is equal to or less than a predetermined value (step S230). It is desirable that the peripheral structure to be extracted is around the target 2 as much as possible.

More specifically, a simulated X-ray fluoroscopic image 13A as shown in FIG. 3 is created from a three-dimensional CT image at a certain respiratory phase. The target 2 and peripheral structures 3A, 3B, 3C, and 3D are extracted from the simulated fluoroscopic image 13A.

Further, a simulated X-ray fluoroscopic image 13B as shown in FIG. 4 is created from a three-dimensional CT image at a respiratory phase different from that of the three-dimensional CT image from which the simulated X-ray fluoroscopic image 13A is created. Similarly, the target 2 and the peripheral structures 3A, 3B, 3C, and 3D are extracted from the simulated fluoroscopic image 13B.

The above two simulated X-ray fluoroscopic images 13A and 13B are compared, so that a movement amount of the target 2 and a movement amount of each of the peripheral structures 3A, 3B, 3C, and 3D are obtained.

In the invention, the peripheral structures 3A, 3B, 3C, and 3D extracted by the simulated X-ray fluoroscopic images 13A and 13B do not include tracking markers that are pre-filled in the subject 1 having the target 2 in order to track the target 2.

An example of the peripheral structures 3A, 3B, 3C, and 3D is assumed to be bones or the like in the subject 1, but the peripheral structures are not limited to the bones and are determined after capturing a three-dimensional CT image or creating a simulated fluoroscopic X-ray image.

In addition, a peripheral structure that is not extracted by any one of the two simulated X-ray fluoroscopic images is desirably treated as not existing without obtaining a movement amount.

As shown in FIG. 4, the movement amounts of the peripheral structures 3A and 3D are large with respect to the movement amount of the target 2. On the other hand, the movement amounts of the peripheral structures 3B and 3C are the same as the movement amount of the target 2, and a difference is small. Such peripheral structures 3B and 3C are extracted as tracking peripheral structures, and an image obtained by projecting a two-dimensional region including the tracking peripheral structures is used as a template image.

The template image is created from two or more three-dimensional CT images and the three-dimensional CT image created by interpolation.

A position of the target 2 may be determined by associating a position of the target 2 set on a treatment planning CT image with a matching result between the treatment planning CT image and the three-dimensional CT images for extraction of the simulated X-ray fluoroscopic images acquired immediately before therapy, or may be manually set from the three-dimensional CT images.

A range to be extracted as a template may be set manually, or may be automatically determined from a preset size.

The created template image is transmitted to the two-dimensional matching apparatus 32 and held therein.

A template image creation processing method by the template creation apparatus 34 is not limited to the flow described above. Another example will be described below with reference to FIG. 5.

As shown in FIG. 5, first, the template creation apparatus 34 receives an input of three-dimensional CT images (four-dimensional CT images) acquired at two different respiratory phases (step S300).

Thereafter, the template creation apparatus 34 extracts the target 2 and the peripheral structures 3A, 3B, 3C, and 3D from the two or more different three-dimensional CT images (step S310).

After that, the template creation apparatus 34 performs deformation positioning by associating reference positions of the two three-dimensional CT images and interpolating a three-dimensional CT image between the two respiratory phases (step S320). The interpolation method is not particularly limited, and various known methods can be used.

Next, the template creation apparatus 34 obtains movement amounts of the target 2 and the peripheral structures 3A, 3B, 3C, and 3D based on the interpolated three-dimensional CT image (step S330).

Thereafter, the template creation apparatus 34 extracts the peripheral structures 3B and 3C having the same level of movement as the target 2 among the peripheral structures 3A, 3B, 3C, and 3D as tracking peripheral structures (step S340). An extraction criterion is preferably the same as that in step S230 described with reference to FIG. 3.

Although two tracking peripheral structures are described as the peripheral structures 3B and 3C, the number of the tracking peripheral structures may be at least one, and the number is not particularly limited.

Although the peripheral structures 3B and 3C whose differences of movement amount with the extracted target 2 are equal to or less than a predetermined value are described as the tracking peripheral structures, a peripheral structure in which a difference between the movement amount of the extracted target 2 and a movement amount of the peripheral structure is the smallest or an arbitrary number of peripheral structures from those having small differences may be regarded as a tracking peripheral structure.

When there is no tracking peripheral structure in which a difference between the movement amount of the extracted target 2 and the movement amount of the peripheral structure is equal to or less than the predetermined value, a peripheral structure with the smallest difference can be set as the tracking peripheral structure. Accordingly, it is possible to avoid a situation in which no tracking peripheral structure is extracted.

Further, when there is no tracking peripheral structure in which the difference between the movement amount of the extracted target 2 and the movement amount of the peripheral structure is equal to or less than the predetermined value, the movement amount of the target 2 and the movement amount of the peripheral structure may be extracted again from the three-dimensional CT images having different respiratory phases. This also makes it possible to avoid a situation in which no tracking peripheral structure is extracted.

Figure 6:
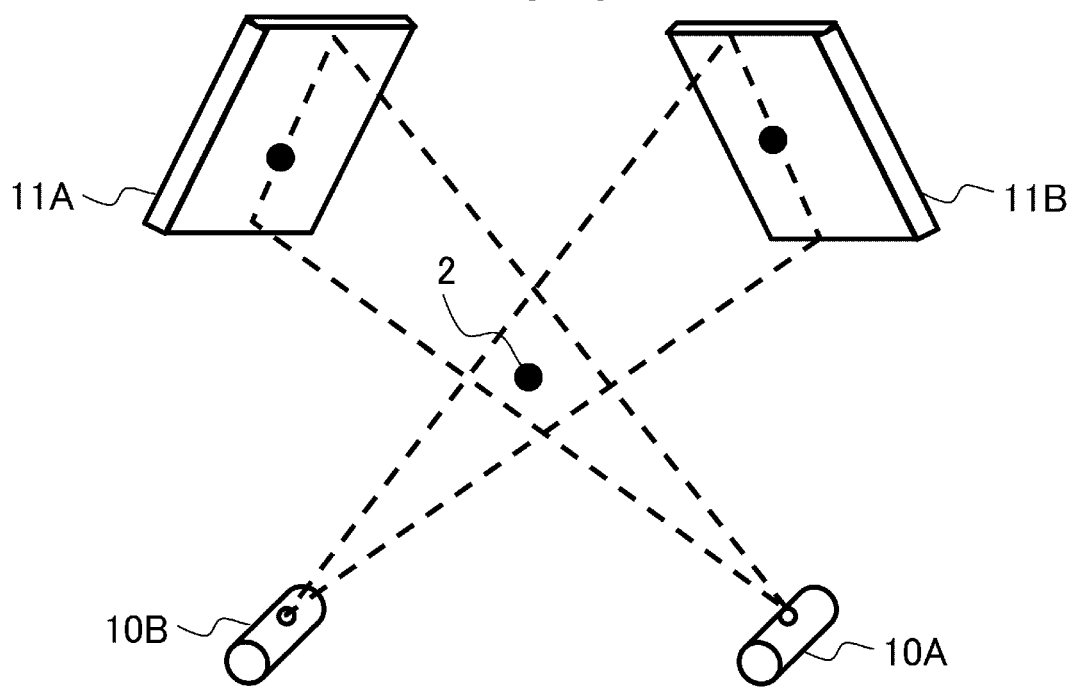
FIG. 6 is a schematic diagram of acquiring a fluoroscopic image by the moving body tracking apparatus according to the embodiment.

In an irradiation step of a therapeutic particle beam, as shown in FIG. 6, the X-ray capturing apparatus 31 irradiates the target 2 with a fluoroscopic X-ray generated from the X-ray tube 10A, and the target 2 is captured by measuring two-dimensional dose distribution of the fluoroscopic X-ray that has passed through the target 2 with the detector 11A. At the same time, a fluoroscopic X-ray generated from the X-ray tube 10B is radiated toward the target 2 and the target 2 is captured by measuring two-dimensional dose distribution of the fluoroscopic X-ray that has passed through the target 2 with the detector 11B. FIG. 6 is a schematic diagram for acquiring an X-ray fluoroscopic image.

The acquisition of the X-ray fluoroscopic image by the fluoroscopic X-ray is implemented intermittently at regular intervals of 30 Hz, for example.

The two-dimensional matching apparatus 32 and the three-dimensional position detection apparatus 33 of the moving body tracking control apparatus 30A calculate a three-dimensional position of the target 2 from two fluoroscopic images acquired via the X-ray capturing apparatus 31, and determine whether to permit radiation of the therapeutic particle beam based on a result thereof.

Specifically, the two-dimensional matching apparatus 32 specifies a timing at which the peripheral structures 3B and 3C in the two fluoroscopic images acquired via the X-ray capturing apparatus 31 most match a template created by the template creation apparatus 34, and specifies projection positions of the target 2 on the detectors 11A and 11B.

As a method for evaluation, image similarity such as normalized correlation coefficient is used. A search uses the entire screen search or a method of searching only in a set search region.

The projection position of the target 2 in each X-ray fluoroscopic image obtained by the matching is transmitted to the three-dimensional position detection apparatus 33.

The three-dimensional position detection apparatus 33 obtains a three-dimensional position of the target 2 from the projection position of the target 2 in each X-ray fluoroscopic image obtained by the matching by the two-dimensional matching apparatus 32. The obtained three-dimensional position is transmitted to the irradiation control apparatus 40.

Figure 7:
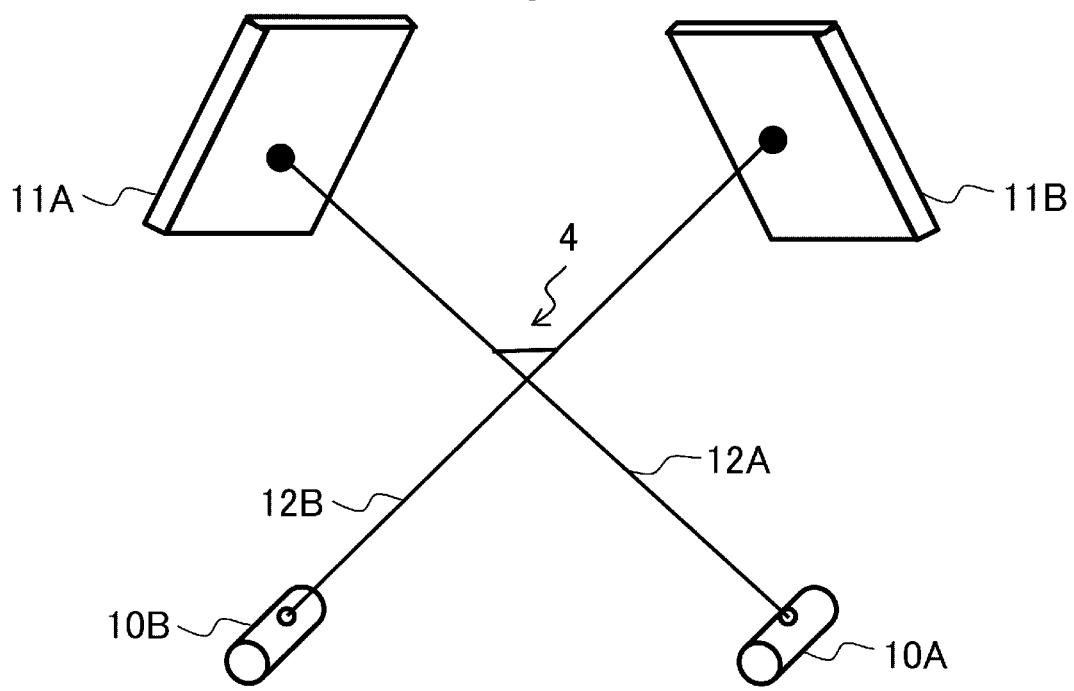
FIG. 7 is a schematic diagram in which the moving body tracking apparatus according to the embodiment calculates a target position from a fluoroscopic image.

FIG. 7 shows a line 12A connecting the position of the target 2 on the detector 11A and the X-ray tube 10A, and a line 12B connecting the position of the target 2 on the detector 11B and the X-ray tube 10B. The two lines obtained by the processing by the three-dimensional position detection apparatus 33 ideally intersect at one point and the intersection is a position where the target 2 is located.

However, in practice, due to an influence of a detection error or an installation error of a fluoroscopic X-ray detector, the two lines do not normally intersect and are in a twisted relationship. A common vertical line can be drawn in a position where the two lines in the twisted relationship are closest to each other. The above common vertical line is referred to as a common vertical line 4. Usually, the three-dimensional position detection apparatus 33 obtains a midpoint of the common vertical line 4 as the three-dimensional position of the target 2.

Returning to FIG. 1, the irradiation control apparatus 40 is connected to the therapeutic radiation irradiation apparatus 50 and the moving body tracking apparatus 30, and controls operation of each device constituting the therapeutic radiation irradiation apparatus 50. The irradiation control apparatus 40 according to the present embodiment controls irradiation of a therapeutic radiation to the target 2 based on a signal from the moving body tracking apparatus 30.

The irradiation control apparatus 40 controls irradiation operation of the therapeutic radiation by the therapeutic radiation irradiation apparatus 50 based on the obtained three-dimensional position of the target 2.

For example, the irradiation control apparatus 40 determines whether or not the position of the target 2 is within a predetermined gate range. When it is determined that the target position in within the gate range, a gate-on signal is transmitted to the irradiation control apparatus 40 to permit radiation of the particle beams to the target 2. On the other hand, when it is determined that the position of the target 2 is not within the gate range, a gate-off signal is transmitted and the radiation is not permitted.

As described above in Patent Literature 1, when control is performed such that the therapeutic radiation is radiated only when the position of the target 2 at the time of treatment planning is completely matched with a position where the therapeutic radiation is to be radiated, treatment time is greatly increased.

In the invention, since it is possible to quantitatively grasp a spatial position deviation amount of the target 2, the irradiation control apparatus 40 sets a region of about ±2 mm from a treatment planning position, and performs gate irradiation of radiating the therapeutic radiation only when the spatial position deviation amount is within the region. Although the target position may deviate from the planning by the above region, irradiation accuracy is ensured by expanding the irradiation range of the therapeutic radiation so as to compensate for the region since the deviation amount can be evaluated and controlled.

As described above, the three-dimensional position of the target 2 is acquired in real time and the three-dimensional gate irradiation is performed, so that both high irradiation accuracy to the target and short irradiation time can be achieved.

Each apparatus in the irradiation control apparatus 40 and the moving body tracking control apparatus 30A described above as well as the X-ray capturing apparatus 31 can be implemented by loading programs into a computer and a Field-Programmable Gate Array (FPGA) including a CPU, a memory, an interface, etc. and executing the calculation. The programs are stored in an internal storage medium or an external storage medium (not shown) in each configuration, and are read and executed by the CPU.

Control processing for operation of each apparatus in the irradiation control apparatus 40 and the moving body tracking control apparatus 30A as well as the X-ray capturing apparatus 31 may be collected into a single program, divided into a plurality of programs, or a combination thereof. A part or all of the programs may be implemented by dedicated hardware or may be modularized. Further, various programs may be installed in each apparatus from a program distribution server, an internal storage medium, or an external storage medium.

Each apparatus in the irradiation control apparatus 40 and the moving body tracking control apparatus 30A as well as the X-ray capturing apparatus 31 are not necessarily independent and two or more of them may be integrated or shared, and only the processing may be shared. In addition, at least a part of the configuration may be connected via a wired or wireless network.

For example, although a case is described in which the irradiation control apparatus 40 side determines whether or not the therapeutic radiation can be radiated, the moving body tracking control apparatus 30A side may determine whether or not the therapeutic radiation can be radiated and output an irradiation permission signal and a non-permission signal to the irradiation control apparatus 40 so that the irradiation control can be performed in the irradiation control apparatus 40.

Next, a procedure of radiation beam irradiation processing by the radiation therapy system including a moving body tracking method according to the present embodiment will be described with reference to FIG. 8. FIG. 8 is a flowchart showing a processing procedure of the radiation therapy system.

First, based on an instruction from an operator, a three-dimensional CT image of the subject 1 lying on the bed 60 for therapeutic radiation irradiation is captured by the CT capturing apparatus 20 (step S90). At this time, three-dimensional CT images of as possible as different respiratory phases are captured at two or more different timings. The captured three-dimensional CT images are transmitted to the template creation apparatus 34.

Thereafter, the template creation apparatus 34 calculates a simulated projection image that simulates capturing of each X-ray capturing apparatus 31 from the two or more three-dimensional CT images captured in step S90. Further, the template creation apparatus 34 calculates a projection position of the target 2 on the simulated projection image, and extracts a periphery thereof as a template (step S100).

Here, the simulated projection image can be created with a relatively fine number of phases by being created from an interpolation image between two or more different respiratory phases of three-dimensional CT images. Here, the interpolation image is a three-dimensional image that reproduces a CT image at a respiratory phase between a captured respiratory phase and another respiratory phase using deformation information including deformation amounts of the target 2 and the peripheral structures 3A, 3B, 3C, and 3D between the two or more different respiratory phases of three-dimensional CT images. It is also possible to use an optimal one from simulated projection images created with the above fine phase number for template creation.

The extracted template is transmitted to the two-dimensional matching apparatus 32.

The method of creating the template in step S100 is preferably performed by the flow as shown in FIGS. 2 and 5 described above. The step S100 corresponds to a step of creating a simulated X-ray fluoroscopic image from a CT image including the target 2 and a step of creating a two-dimensional region including the target 2 from the simulated fluoroscopic image as a template.

Thereafter, when the operator gives an instruction to start fluoroscopic X-ray capturing, the X-ray capturing apparatus 31 of the moving body tracking apparatus 30 intermittently starts X-ray capturing (step S110). The X-ray capturing is continued until the therapy is completed or the operator performs stop operation.

Thereafter, the X-ray image is captured and the acquired X-ray fluoroscopic image is transmitted to the two-dimensional matching apparatus 32 (step S120).

The steps S110 and S120 correspond to a step of acquiring X-ray fluoroscopic images including the target 2 from at least two directions.

After that, the two-dimensional matching apparatus 32 performs two-dimensional matching between the X-ray fluoroscopic image captured in steps S110 and S120 and the template image created in step S100 to specify a position of the target 2 in the fluoroscopic image (step S130). The specified position of the target 2 is transmitted to the three-dimensional position detection apparatus 33.

The step S130 corresponds to a step of matching the at least two X-ray fluoroscopic images with a template.

After that, the three-dimensional position detection apparatus 33 calculates a three-dimensional position of the target 2 based on a plurality of two-dimensional matching positions specified in step S130 (step S140). The obtained three-dimensional position is transmitted to the irradiation control apparatus 40.

The step S140 corresponds to a step of obtaining a three-dimensional position of the target 2 from a plurality of matching results.

Thereafter, the irradiation control apparatus 40 determines whether or not therapy irradiation is started by the operator (step S145). When it is determined that the start operation has not been performed, the processing returns to step S120 that is the X-ray capturing step. On the other hand, when it is determined that the therapy irradiation start operation has been performed, the processing moves to step S150.

After that, the irradiation control apparatus 40 radiates the therapeutic radiation only when the position of the target 2 is within a gate region based on the three-dimensional position of the target 2 obtained in step S140 (step S150).

Thereafter, the irradiation control apparatus 40 determines whether or not irradiation of a preset therapeutic beam is completed (step S160). When it is determined that the irradiation of the preset therapeutic beam is not completed, the processing returns to step S120. On the other hand, when it is determined that the irradiation of the therapeutic beam is completed, the fluoroscopic X-ray capturing is completed and the procedure ends.

Next, an effect of the present embodiment will be described.

The radiation therapy system 100 includes the therapeutic radiation irradiation apparatus 50 that generates and radiates radiation, the moving body tracking apparatus 30 that obtains a three-dimensional position of the target 2 and tracks movement thereof, and the irradiation control apparatus 40 that controls irradiation of the therapeutic radiation to the target by controlling the therapeutic radiation irradiation apparatus 50 based on a signal from the moving body tracking apparatus 30.

The moving body tracking apparatus 30 includes the fluoroscopic apparatus that acquires X-ray fluoroscopic images including the target 2 from at least two directions, and the moving body tracking control apparatus 30A that obtains a position of the target 2 from the X-ray fluoroscopic images acquired by the fluoroscopic apparatus. The moving body tracking control apparatus 30A creates a simulated X-ray fluoroscopic image from the CT images including the target 2, creates a two-dimensional region including the target 2 from the simulated X-ray fluoroscopic image as a template, matches each of at least two X-ray fluoroscopic images with the template, and obtains a three-dimensional position of the target 2 from a plurality of matching results.

In general, a target in radiation therapy does not have contrast on a fluoroscopic image and is difficult to directly visually recognize. As a result, when an image of only the target 2 is used as the template image, it is difficult to accurately detect the position by matching.

In contrast, in the invention, by using a two-dimensional region around the target 2 as a template, matching can be performed based on the peripheral structures 3A, 3B, 3C, and 3D having higher contrast than the target 2. If a positional relationship between the peripheral structures 3A, 3B, 3C, and 3D and the target 2 is maintained, a state in which the peripheral structures 3A, 3B, 3C, and 3D are matched is a state in which the target 2 is also matched. In this way, the three-dimensional position of the target 2 that is difficult to visually recognize from the X-ray fluoroscopic images can be detected in real time based on the peripheral structures 3A, 3B, 3C, and 3D.

Since such an effect is obtained, in particular, by providing an irradiation allowable range for the position of the target 2 and applying the irradiation allowable range to a radiation therapy system that performs gate irradiation to irradiate therapeutic radiation when the position of the target 2 is within the irradiation allowable range, which is a method of increasing irradiation time, therapy can be finished in a short time while irradiating the target 2 precisely.

The moving body tracking control apparatus 30A creates a four-dimensional CT image from two or more three-dimensional CT images, obtains a movement amount of the target 2 and movement amounts of the peripheral structures 3A, 3B, 3C, 3D from the four-dimensional CT image, extracts the peripheral structure 3A, 3B, 3C, 3D in which a difference between the obtained movement amount of the target 2 and the movement amounts of the peripheral structures 3A, 3B, 3C, 3D is equal to or less than a predetermined value as a tracking peripheral structure, and sets a two-dimensional region including the tracking peripheral structure as a template. Accordingly, since only the peripheral structures 3B and 3C having a small positional relationship with the target 2 are present on the template, the three-dimensional position of the target 2 determined from the peripheral structures 3B and 3C can be obtained with higher accuracy. This makes it possible to finish the therapy in a short time while irradiating the target 2 more precisely.

Further, the moving body tracking control apparatus 30A extracts the target 2 and the peripheral structures 3A, 3B, 3C, and 3D from each of two or more three-dimensional CT images, obtains movement amounts of the extracted target 2 and the peripheral structures 3A, 3B, 3C, and 3D from two or more three-dimensional CT images, extracts the peripheral structures 3A, 3B, 3C, and 3D whose difference of movement amount with the target 2 is equal to or less than a predetermined value as a tracking peripheral structure, and sets a two-dimensional region including the tracking peripheral structure as a template. Therefore, this makes it possible to finish therapy in a short time while irradiating the target 2 more precisely.

In addition, since the peripheral structures 3A, 3B, 3C, and 3D do not include tracking markers that are pre-filled in the subject 1 having the target 2 in order to track the target 2, labor and burden of filling the markers can be reduced and the treatment time can be further shortened.

Further, the moving body tracking control apparatus 30A calculates a deformation amount from two or more different three-dimensional CT images, creates an interpolation image between a plurality of three-dimensional CT images, and creates a simulated fluoroscopic image based on the interpolation image. Since it is possible to use an optimum one from simulated projection images created with a fine number of phases for template creation, matching accuracy can be further improved.

The moving body tracking apparatus 30 further includes the bed 60 on which the subject 1 having the target 2 is placed, and the CT capturing apparatus 20 that is installed in a therapy room in which the bed 60 is accommodated and that captures a CT image that is a basis for creating a simulated fluoroscopic image. The moving body tracking apparatus 30 creates a simulated fluoroscopic image from the three-dimensional CT image captured by the CT capturing apparatus 20 immediately before the irradiation of therapeutic radiation.

As shown in step 100 of FIG. 8, when the CT image is captured and the template is created immediately before the therapy, a positional relationship between the position of the target 2 in the template and the peripheral structures 3B and 3C can hardly change and is considered to be maintained during the therapy.

Therefore, by determining the position of the target 2 by the template created based on the projection image created from CT immediately before the therapy, even when it is difficult to visually recognize the target 2 on the X-ray fluoroscopic image, the three-dimensional position of the target can be determined with higher accuracy based on the peripheral structure. In particular, by performing gate irradiation in accordance with the three-dimensional position, it is possible to perform highly accurate therapeutic radiation irradiation to the target 2 and a short-time therapy.

OTHER EMBODIMENTS

The invention is not limited to the above embodiment and various modifications and applications can be made thereto. For example, the above-described embodiment has been described in detail in order to make the invention easy to understand, and the invention is not necessarily limited to those having all the configurations described.

What is claimed is:

1. A moving body tracking apparatus that obtains a three-dimensional position of a target and tracks movement of the target, the moving body tracking apparatus comprising:
    a fluoroscopic apparatus that acquires fluoroscopic images including the target from at least two directions; and
    a moving body tracking control apparatus that obtains a position of the target from the fluoroscopic images acquired by the fluoroscopic apparatus, wherein
    the moving body tracking control apparatus:
        creates a simulated fluoroscopic image from a CT image including the target,
        creates a two-dimensional region including the target from the simulated fluoroscopic image as a template,
        matches each of at least two fluoroscopic images with the template, and
        obtains the three-dimensional position of the target from a plurality of matching results,
    wherein the moving body tracking control apparatus creates a four-dimensional CT image from two or more three-dimensional CT images, obtains a movement amount of the target and movement amounts of peripheral structures from the four-dimensional CT image, extracts a peripheral structure in which a difference between the obtained movement amount of the target and movement amounts of the peripheral structures is equal to or less than a predetermined value as a tracking peripheral structure, and sets the two-dimensional region including the tracking peripheral structure as a template.

2. A moving body tracking apparatus that obtains a three-dimensional position of a target and tracks movement of the target, the moving body tracking apparatus comprising:
    a fluoroscopic apparatus that acquires fluoroscopic images including the target from at least two directions; and
    a moving body tracking control apparatus that obtains a position of the target from the fluoroscopic images acquired by the fluoroscopic apparatus, wherein
    the moving body tracking control apparatus:
        creates a simulated fluoroscopic image from a CT image including the target,
        creates a two-dimensional region including the target from the simulated fluoroscopic image as a template,
        matches each of at least two fluoroscopic images with the template, and
        obtains the three-dimensional position of the target from a plurality of matching results,
    wherein the moving body tracking control apparatus extracts the target and peripheral structures from each of two or more three-dimensional CT images, obtains movement amounts of the extracted target and the peripheral structures from the two or more three-dimensional CT images, extracts a peripheral structure whose difference in movement amount with the target is equal to or less than a predetermined value as a tracking peripheral structure, and set the two-dimensional region including the tracking peripheral structure as a template.

3. The moving body tracking apparatus according to claim 1, wherein
    the peripheral structures do not include tracking markers that are pre-filled in a subject having the target to track the target.

4. The moving body tracking apparatus according to claim 1, wherein
    the moving body tracking control apparatus calculates a deformation amount from the three-dimensional CT images of two or more different phases, creates an interpolation image between a plurality of three-dimensional CT images, and creates a simulated fluoroscopic image based on the interpolation image.

5. A radiation therapy system comprising:
    an irradiation apparatus that generates and radiates radiation;
    the moving body tracking apparatus according to claim 1; and
    an irradiation control apparatus that controls irradiation of therapeutic radiation to a target by controlling the irradiation apparatus based on a signal from the moving body tracking apparatus.

6. The radiation therapy system according to claim 5, further comprising:
    a bed on which a subject having the target is placed; and
    a CT capturing apparatus that is installed in a therapy room in which the bed is accommodated and that captures a CT image that is a basis for creating the simulated fluoroscopic image, wherein
    the moving body tracking apparatus creates the simulated fluoroscopic image from a three-dimensional CT image captured by the CT capturing apparatus immediately before irradiation of therapeutic radiation.

7. A moving body tracking method that tracks movement of a target, the moving body tracking method comprising:
    acquiring fluoroscopic images including the target from at least two directions;
    creating a simulated fluoroscopic image from a CT image including the target;
    creating a two-dimensional region including the target from the simulated fluoroscopic image as a template;
    performing matching of each of at least two or more of the fluoroscopic images with the template;
    obtaining a three-dimensional position of the target from a plurality of matching results,
    creating a four-dimensional CT image from two or more three-dimensional CT images, obtaining a movement amount of the target and movement amounts of peripheral structures from the four-dimensional CT image, extracting a peripheral structure in which a difference between the obtained movement amount of the target and movement amounts of the peripheral structures is equal to or less than a predetermined value as a tracking peripheral structure, and setting the two-dimensional region including the tracking peripheral structure as a template.

8. The moving body tracking method according to claim 7, wherein
    obtaining the CT image including the target is performed immediately before obtaining the three-dimensional position of the target.

9. The moving body tracking apparatus according to claim 2, wherein the peripheral structures do not include tracking markers that are pre-filled in a subject having the target to track the target.

10. The moving body tracking apparatus according to claim 2, wherein the moving body tracking control apparatus calculates a deformation amount from the three-dimensional CT images of two or more different phases, creates an interpolation image between a plurality of three-dimensional CT images, and creates a simulated fluoroscopic image based on the interpolation image.

11. A radiation therapy system comprising:
an irradiation apparatus that generates and radiates radiation;
the moving body tracking apparatus according to claim 2; and
an irradiation control apparatus that controls irradiation of therapeutic radiation to a target by controlling the irradiation apparatus based on a signal from the moving body tracking apparatus.

* * * * *